United States Patent [19]

Tomasso

[11] Patent Number: 5,322,668
[45] Date of Patent: Jun. 21, 1994

[54] LOCKED BOTTLE HOLDER

[75] Inventor: David A. Tomasso, Rochester, N.Y.

[73] Assignee: Eastman Kodak Company, Rochester, N.Y.

[21] Appl. No.: 86,408

[22] Filed: Jul. 1, 1993

[51] Int. Cl.$^5$ .............................................. B01L 9/00
[52] U.S. Cl. ................................... 422/104; 206/446; 211/74; 422/102
[58] Field of Search .................. 422/102, 104, 64, 65; 206/446; 211/74, 76

[56] References Cited

U.S. PATENT DOCUMENTS

| | | | |
|---|---|---|---|
| 4,849,177 | 7/1989 | Jordan | 422/64 |
| 4,853,188 | 8/1989 | Toya | 422/104 |
| 5,075,082 | 12/1991 | Fechtner | 422/102 |
| 5,137,693 | 8/1992 | Mawhirt | 422/104 |
| 5,246,665 | 9/1993 | Tyranski et al. | 422/64 |

Primary Examiner—James C. Housel
Assistant Examiner—Laura E. Collins
Attorney, Agent, or Firm—Dana M. Schmidt

[57] ABSTRACT

A bottle holder for restrictively holding two bottles in prescribed positions, comprising a base, a top member, and a side wall, the bottles being mounted between the base and top member. The holder is improved in that there are provided a rail and groove sliding fit of the top member and side wall, and an interlock fit wherein a tooth on one of the top member and side wall slides over a ledge until it fits under the ledge in a locking manner to prevent disassembly.

7 Claims, 3 Drawing Sheets

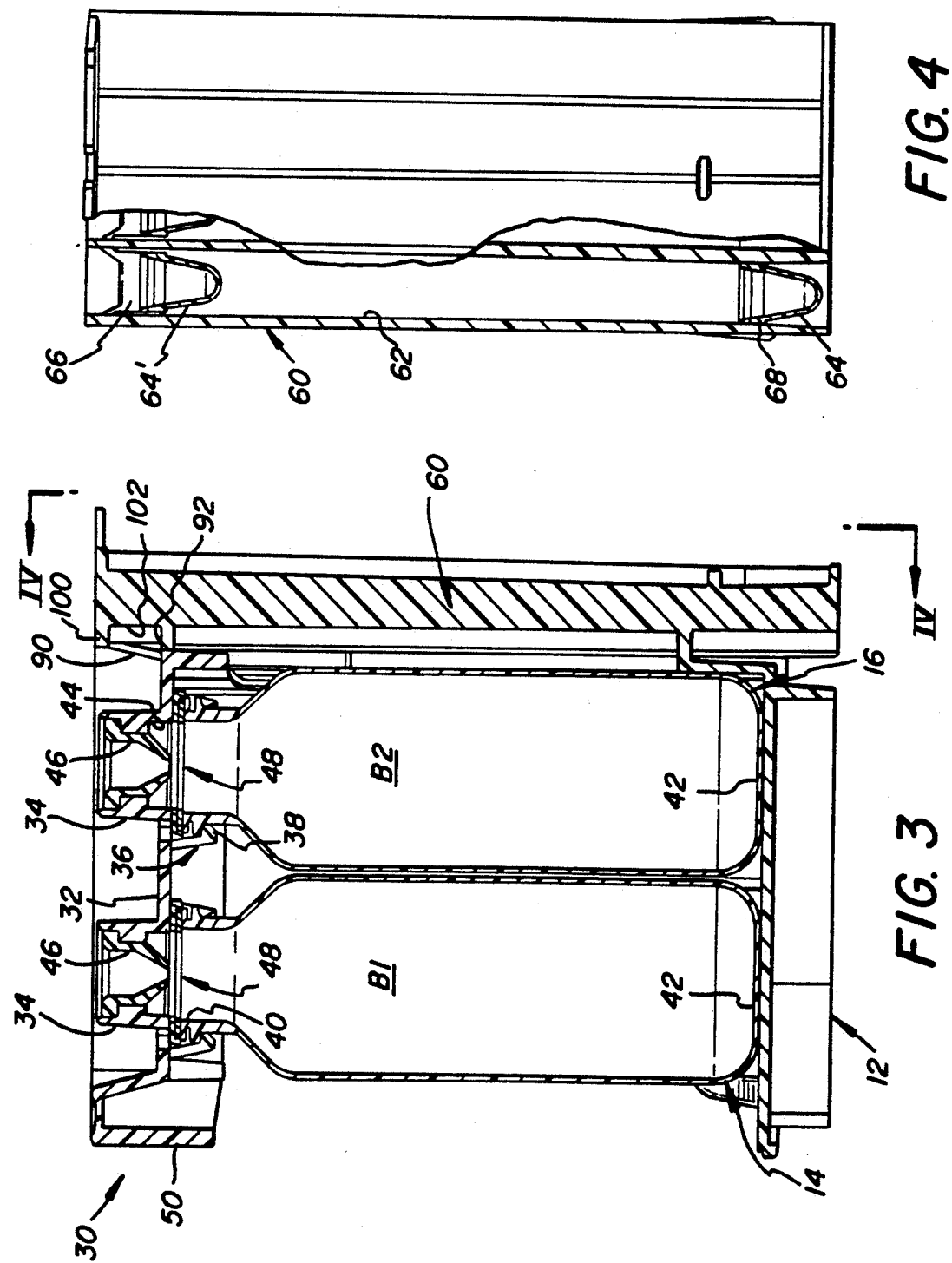

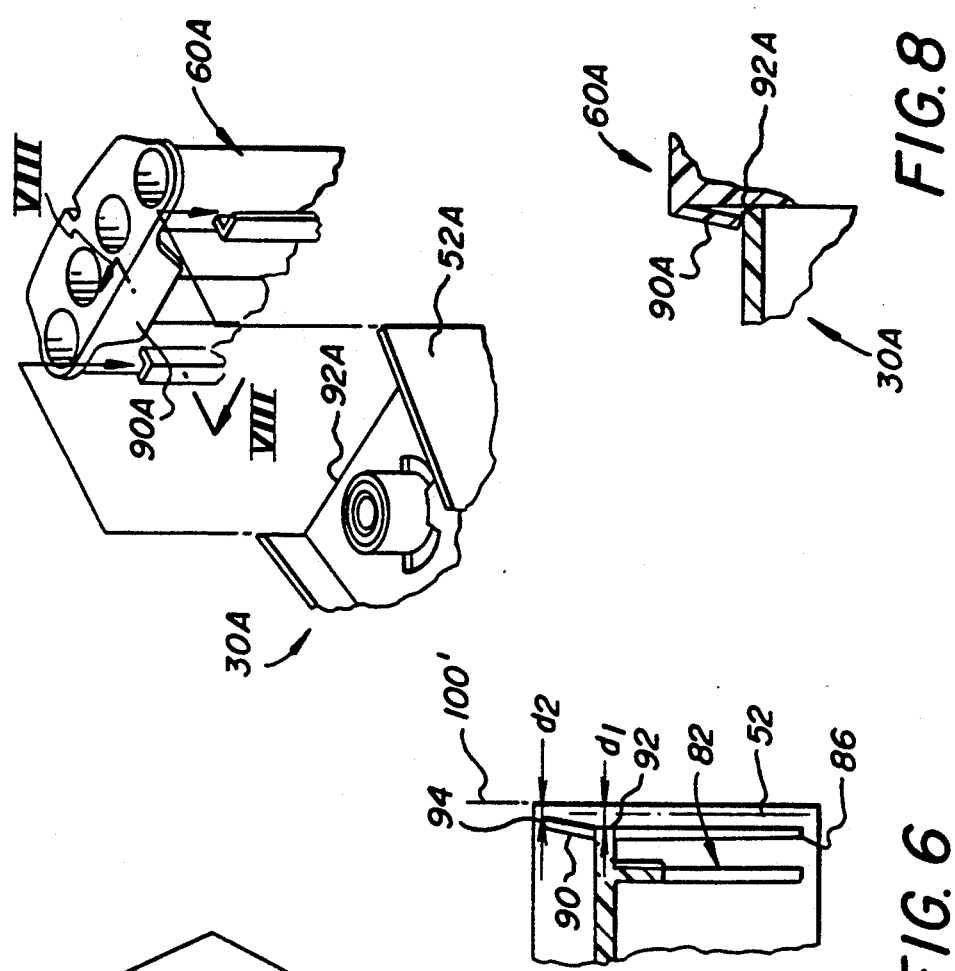
FIG. 7
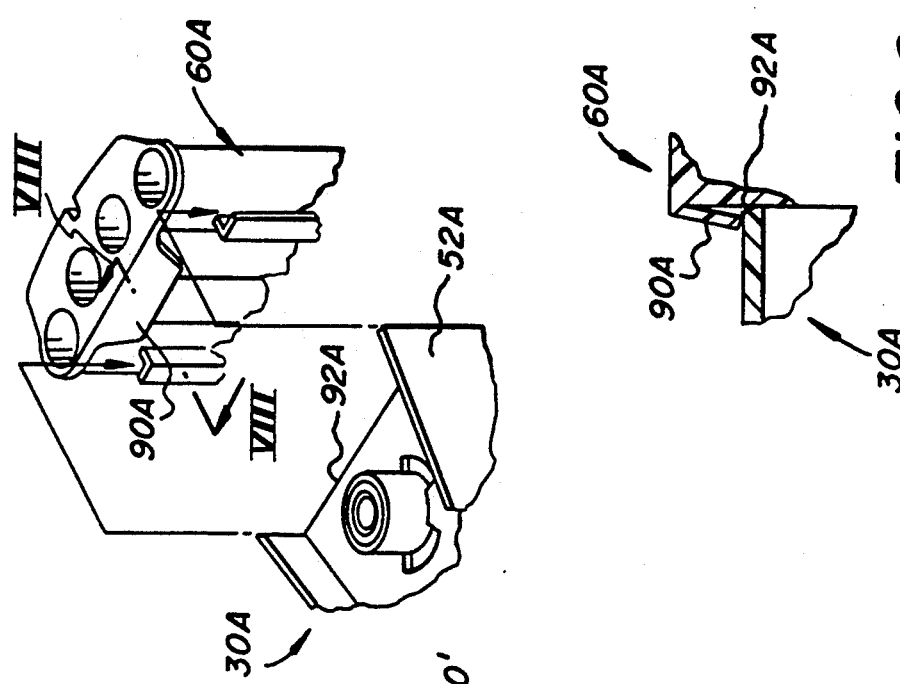
FIG. 8
FIG. 6
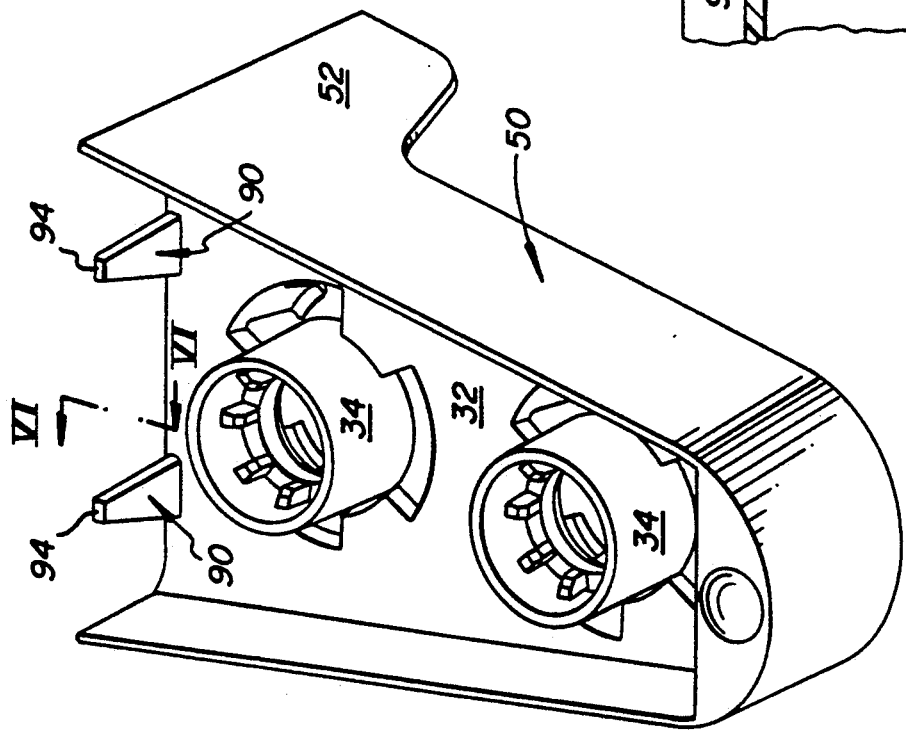
FIG. 5

5,322,668

LOCKED BOTTLE HOLDER

FIELD OF THE INVENTION

The invention relates to a holder for reagent bottles, as may be used in an analyzer.

BACKGROUND OF THE INVENTION

In an automated analyzer using liquid reagents in a reaction cuvette to assay for an analyte in a patient sample liquid, it is conventional to supply the different reagents from a plurality of different bottles held in a bottle holder. An example is shown in U.S. Pat. No. 5,075,082. In such a holder, it is important that each bottle be kept at its prescribed position and that the user not be able to re-position (i.e., switch) the bottles, either deliberately or by accident, lest the analyzer withdraw the wrong reagent from a given position in the holder. Such bottle position integrity is maintained by the construction shown in said '082 patent by reason of a) the size differences between the bottles and the construction of the holder to receive only those sizes, and b) the use of welding (column 4, lines 14-19) to integrate the holder so that it cannot be later reopened and the bottles re-positioned.

However, it is preferred that identical bottle sizes be available, rather than distinguishing positions in the holder solely by bottle size. This allows for bottle interchangeability, when filling the bottles during manufacturing. Further, a construction that requires the parts to be welded together to prevent bottle re-positioning, is obviously more expensive than a construction assembled simply by sliding parts together. However, any assembly by sliding can be undone by reversing the sliding, thus making it easy for a user to re-position the bottles.

Therefore, there has been a need prior to this invention to provide a bottle holder for use as described, which is more readily assembled than is possible by welding, and yet ensures substantial permanence in the assembly to prevent bottle re-positioning.

SUMMARY OF THE INVENTION

The present invention provides a bottle holder that meets the aforesaid need.

More specifically, there is provided a bottle holder for holding at least two bottles of differing substances in prescribed positions, each bottle having a bottom end and an access end, the holder comprising a base with at least one recess therein shaped to retain the bottom end of the bottles, a top member disposed above and opposite the base and having at least one recess therein shaped to retain the access ends of the bottles, and a side wall extending between and joining together the base and the top member. The holder is improved in that the top member and the side wall further comprise an interlock shaped to substantially permanently secure the top member to the side wall with the bottles within the recesses, the interlock further including a) on one of the top member and the side wall at least one locking tooth biased to project out beyond a portion of one of the top member and the side wall, and b) on the other of the top member and the side wall, a recess bounded by a ledge, the top member and the side wall further including sliding means for sliding one onto the other so that the at least one tooth slides past the ledge into the recess into a substantially permanent locked configuration and the bottles can not be re-positioned.

Accordingly, it is an advantageous feature of the invention that a bottle holder for more than one bottle or reagents is easily assembled into a substantially permanent assembly so that the bottles therein cannot be readily switched in their positions. (As used herein, "substantially permanent" means without breaking the holder or destroying any part thereof.)

Other advantageous features will become apparent upon reference to the attached Detailed Description, when read in light of the attached drawings.

BRIEF DESCRIPTION OF THE DRAWINGS

FIG. 3 is a section view taken vertically generally along the line III—III of FIG. 1;

FIG. 4 is an elevational view, partially broken away, along line IV—IV of FIG. 3;

FIG. 5 is an isometric view of the top member shown in FIG. 1;

FIG. 6 is a fragmentary vertical section view taken along the line VI—VI of FIG. 5;

FIG. 7 is a fragmentary, exploded view prior to assembly, of an alternate embodiment of the invention; and FIG. 8 is a fragmentary vertical section view of the side wall taken along the line VIII—VIII of FIG. 7.

DESCRIPTION OF THE PREFERRED EMBODIMENTS

The description which follows features the preferred embodiments, in which two plastic bottles of two different liquid reagents are disposed lengthwise along an elongated bottle holder that also contains a plurality of reaction cuvettes each pre-supplied with antibody reagents, in a plurality of stacks. In addition, the invention is applicable regardless of the number, kind, or position of the bottles (as long as there are at least two), and regardless whether reaction cuvettes are also stacked or in any way contained within the holder and/or themselves have any reagents in them.

Orientations such as "above", "below", "top", "side" and the like refer to the orientation of the parts in their intended use.

Figure 1:
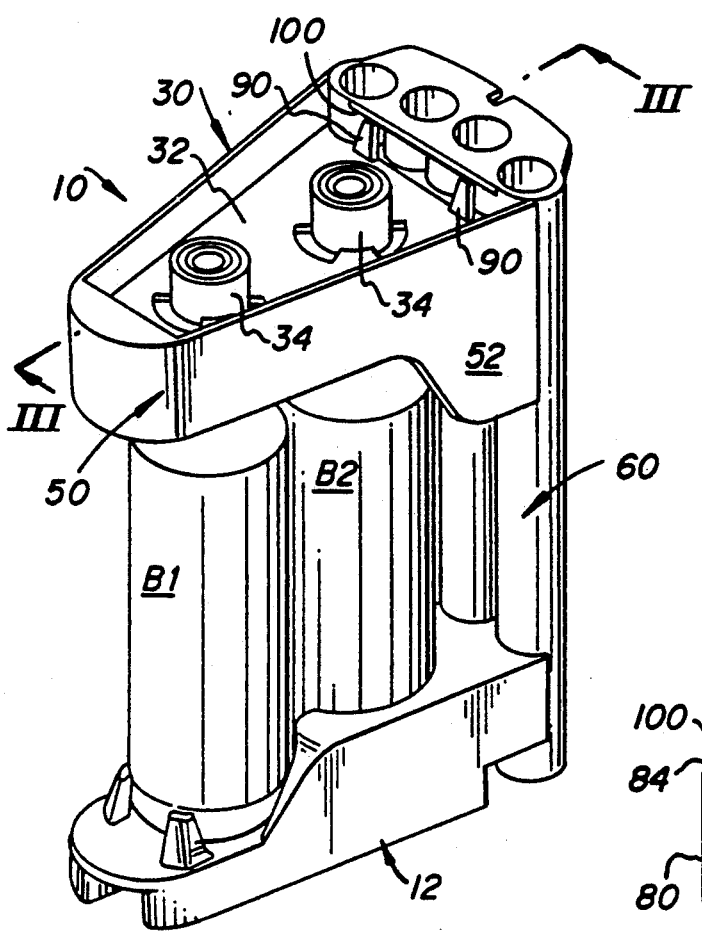
FIG. 1 is an isometric view of a holder constructed in accordance with the invention.

The bottle holder 10 of the invention is generally pie-shaped, FIG. 1, so as to slide in and out of a wet chemistry analyzer, as is conventional, generally in a circular arrangement of such holders. Such a bottle holder 10 comprises, necessarily, a base 12, a top member 30, and a side wall 60 extending between and joined to the base and top member.

Figure 2:
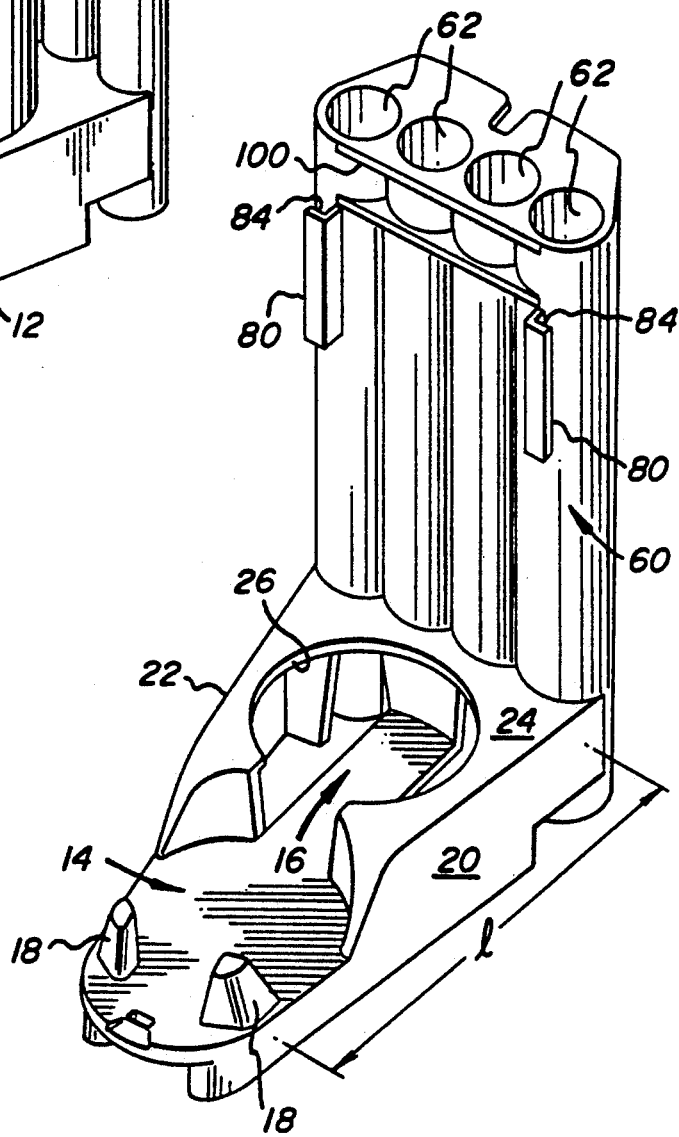
FIG. 2 is an isometric view of the holder of FIG. 1 prior to assembly of the top member.

More precisely, base 12 comprises a platform having at least one recess and preferably recesses 14 and 16, FIG. 2, for each of two bottles B1 and B2 held by holder 10. As is apparent, recesses 14 and 16 are disposed along the length "1" of holder 10, which is the dimension that aligns with a radius of the circular arrangement of such holders in the analyzer (not shown). Recess 14 is partially defined by two upstanding lugs 18. On the other hand, recess 16 is preferably defined by raised side walls 20 and 22 terminating in a top surface 24 in which opening 26 is formed as the top of the recess 16. Base 12 is then joined to side wall 60 by any conventional means, e.g., by welding, by adhesive, by mechanical latches, etc.

Top member 30 comprises a generally flat plate 32 provided with raised bosses 34, FIG. 3, and depending fingers 36 with snap latches 38 for locking under the rim of the access end 40 of a bottle B1 or B2. (Opposite ends 42 of the bottles are retained in recesses 14 and 16). Apertures 44 in bosses 34 are shaped to receive stoppers 46, such as duck-billed stoppers. A foil seal 48 is applied directly to the end 40 of the bottle, before it is inserted into latches 38. A side skirt 50 wraps around plate 32 and terminates in a portion 52, FIG. 1, that extends down along and in contact with side wall 60.

Sidewall 60 can have any desired shape and thickness, but preferably it has a plurality of, e.g., four cylindrical apertures 62 extending the full height of the wall, FIG. 4. A stack of reaction cuvettes 64 is mounted within each aperture, preferably shaped as cups or wells. (Only the uppermost and lowermost cuvettes are shown for clarity). They nest one inside the other, and the uppermost cuvette 64' is preferably topped with a seal cap 66 to seal off the stack from the atmosphere. The bottom of the stack is sealed within the aperture 62 by virtue of the friction fit between a flange 68 of each cuvette 64, and the side wall of the aperture 62.

Optionally, a plastic insert, not shown, can also be inserted into the bottom of apertures 62 prior to insertion of the holder into an analyzer.

In accordance with the invention, a sliding fit is provided between top member 30 and side wall 60, along with an interlock fit once the parts are fully slid together. To that end, FIG. 2, sliding means are provided comprising preferably, two outwardly-directed rails 80 at opposite sides of side wall 60, and a cooperating notch 82 mounted on the inside of each of the two skirt portions 52, FIG. 6. Top edge 84 of rails 80 enters the bottom end 86 of notches 82 so as to permit top member 10 to slide onto side wall 60.

The interlock fit occurs between at least one tooth 90 on one of the top member and side wall, and a ledge 100 on the other. For example, FIG. 1, two teeth 90 extend upwardly and outwardly from edge 92 of plate 32, as shown especially in FIG. 6. The teeth are biased when formed so that upper edges 94 thereof are at a distance "$d_2$" from the ledge 100 (shown as a vertical plane 100', FIG. 6) that is less than the distance "$d_1$" of plate edge 92, to ensure that when edge 92 is resting on side wall 60, FIG. 3, teeth 90 are locked under ledge 100, within recess 102, formed under the ledge. See also FIG. 5. This prevents top member 30 from being slid off side wall 60 and the bottles B1 and B2 being switched by the user.

As will be readily apparent, teeth 90 need not be on the top member and ledge 100 on the side wall, but can be reversed as shown in FIGS. 7 and 8. Parts similar to those previously described bear the same reference numeral to which the distinguishing suffix "A" is appended. Thus, top member 30A is the same as described in the previous embodiment, except that it has no teeth for an interlocking fit. Instead, edge 92A becomes the ledge of the interlocking fit. Sidewall 60A is the same as for the previous embodiments, except that it has a single tooth 90A, which is downwardly depending, rather than upstanding as previously described. Tooth 90A projects outwardly towards the assembled location of top member 30A, FIG. 8, so as to snap over ledge 92A with an interlock fit, once ledge 92A has cleared the tooth.

In like manner, not shown, the rail and notch combination can be switched. That is, the rails can project from skirt portions 52 or 52A to engage corresponding notches on side wall 60 or 60A.

The invention disclosed herein may be practiced in the absence of any element which is not specifically disclosed herein.

The invention has been described in detail with particular reference to certain preferred embodiments thereof, but it will be understood that variations and modifications can be effected within the spirit and scope of the invention.

What is claimed is:

1. In a bottle holder for holding at least two bottles of differing substances in prescribed positions, each bottle having a bottom end and an access end, the holder comprising a base with at least one recess therein shaped to retain the bottom end of the bottles, a top member disposed above and opposite said base and having at least one recess therein shaped to retain the access end of said bottles, and a side wall extending between and joining together said base and said top member, the improvement wherein said top member and said side wall further comprise an interlock shaped to substantially permanently secure said top member to said side wall with said bottles within recesses, said interlock further including a) on one of said top member and said side wall, at least one locking tooth biased to project out beyond a portion of said one of said top member and said side wall, and b) on the other of said top member and said side wall, a recess bounded by a ledge, said recess being shaped and sized to capture said at least one locking tooth under said ledge, said top member and said side wall further including sliding means for sliding one onto the other so that said at least one tooth flexes sufficiently to slide past said ledge and after passing said ledge flexes back into said recess into a substantially permanent locked configuration and said bottles cannot be re-positioned.

2. A holder as defined in claim 1, wherein said sliding means comprise a rail on one of said top member and side wall, and a groove on the other of said top member and side wall, said groove being dimensioned so as to receive said rail therein.

3. A holder as defined in claim 2, wherein said side wall further comprises a cylindrical aperture extending the full height of said side wall.

4. A holder as defined in claim 3, and further including a plurality of reaction cuvettes stacked within said aperture, a seal being provided at one end of the aperture to protect said cuvettes from the environment.

5. A holder as defined in claim 1, wherein said side wall further comprises a cylindrical aperture extending the full height of said side wall.

6. A holder as defined in claim 5, and further including a plurality of reaction cuvettes stacked within said aperture, a seal being provided at one end of the aperture to protect said cuvettes from the environment.

7. A holder as defined in claim 1, wherein said at least one tooth is on said top member.

* * * * *